(12) United States Patent
Wilk

(10) Patent No.: US 7,500,956 B1
(45) Date of Patent: Mar. 10, 2009

(54) APPARATUS AND METHOD FOR RESONANT DESTRUCTION OF TUMORS

(76) Inventor: Peter J. Wilk, 185 W. End Ave., New York, NY (US) 10023

( * ) Notice: Subject to any disclaimer, the term of this patent is extended or adjusted under 35 U.S.C. 154(b) by 568 days.

(21) Appl. No.: 09/342,824

(22) Filed: Jun. 29, 1999

(51) Int. Cl.
*A61N 7/00* (2006.01)

(52) U.S. Cl. .......................................... 601/2; 600/439

(58) Field of Classification Search ................ 600/439; 601/1, 2, 3, 4
See application file for complete search history.

(56) References Cited

U.S. PATENT DOCUMENTS

| | | | | |
|---|---|---|---|---|
| 4,315,514 A | * | 2/1982 | Drewes et al. | 128/653 |
| 4,771,786 A | * | 9/1988 | Iinuma | 128/660.06 |
| 4,819,649 A | * | 4/1989 | Rogers et al. | 128/660.02 |
| 5,099,848 A | * | 3/1992 | Parker et al. | 128/661.07 |
| 5,391,140 A | * | 2/1995 | Schaetzle et al. | 601/4 |
| 5,526,815 A | * | 6/1996 | Granz et al. | 128/660.03 |
| 5,871,446 A | * | 2/1999 | Wilk | 600/407 |
| 5,984,882 A | * | 11/1999 | Rosenschein et al. | 601/2 |

* cited by examiner

*Primary Examiner*—Eleni Mantis Mercader
(74) *Attorney, Agent, or Firm*—R. Neil Sudol; Henry D. Coleman; William J. Sapone

(57) ABSTRACT

In a method for treating cancer, a series of investigatory pressure waves of respective different preselected frequencies are generated in a patient so that the pressure waves are transmitted to a tumor through overlying tissues, while responsive oscillatory motion of the tumor and at least some internal tissues of the patient proximate to the tumor are monitored during this pressure wave generation. From the responsive oscillatory motion of the tumor and the internal tissues, a pressure wave frequency is determined which results in a resonant loading of the tumor and essentially leaves the internal tissues undamaged. Subsequently, treatment pressure waves are generated in the patient and have the determined pressure wave frequency and of an effective amplitude so that the tumor resonates with sufficient energy to mechanically destroy the tumor.

27 Claims, 10 Drawing Sheets

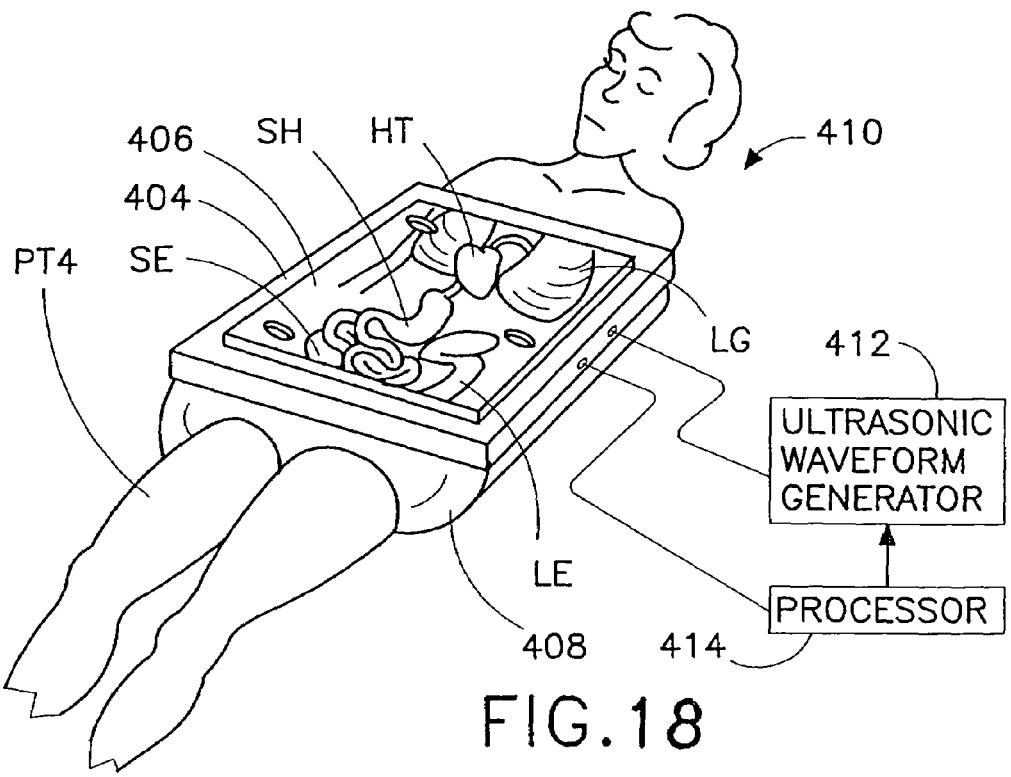
FIG. 18
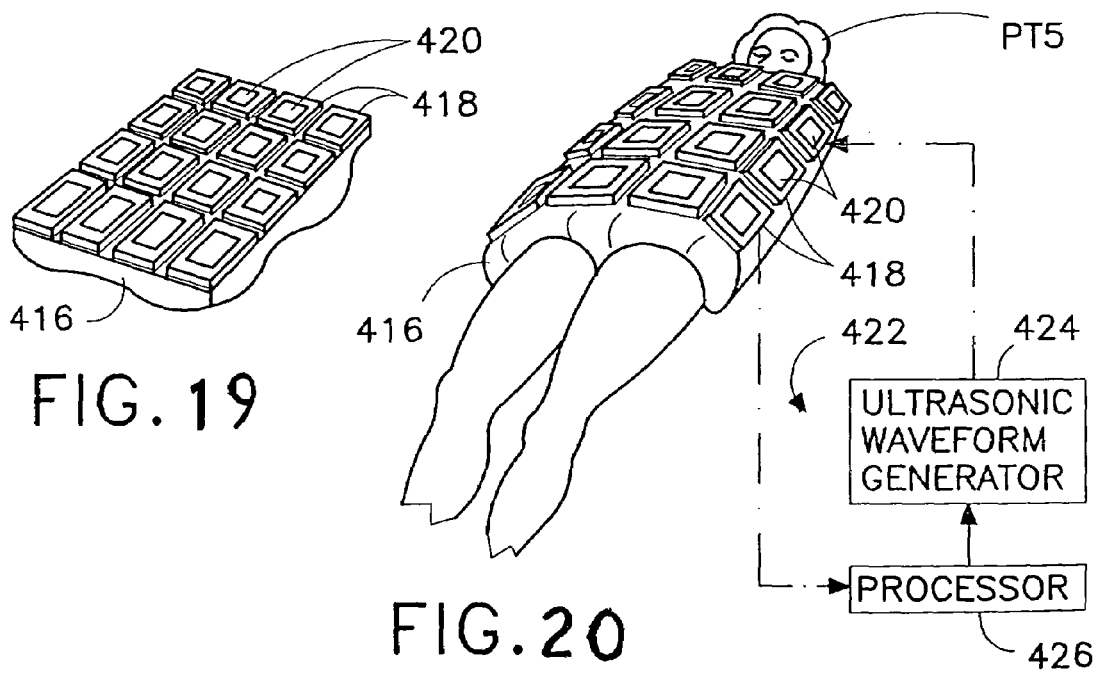
FIG. 19
FIG. 20

APPARATUS AND METHOD FOR RESONANT DESTRUCTION OF TUMORS

BACKGROUND OF THE INVENTION

This invention relates to a medical treatment method and to an associated medical treatment apparatus. More particularly, this invention relates to a method and an associated apparatus for the non-invasive destruction of internal tissues.

Cancer continues to be a scourge of mankind. There is a plethora of techniques for treating cancer. Most of these techniques have dire side effects, generally involving substantial amounts of pain to the patient.

Once cancer has reached the tumor stage, where lumps of cancerous tissues are detectable either directly through touch and vision or indirectly with the aid of MRI and CAT scanners, the principal treatment is surgical. The victim is operated on and the tumor cut out of the body. Frequently, the location and size of the tumor are such that surgical removal results in a severe impairment to the patient's body and lifestyle. For example, surgical removal of a large tumor in a femur frequently results in an amputation.

The operations for surgically removing tumors are nearly universally open incision type operations. These operations are naturally debilitating and require extensive post surgical care. For these reasons, the costs of conventional open incision surgery are enormous.

Although minimally invasive procedures such as laparoscopic or thoracoscopic surgery have increased at geometric rates in frequency of performance, minimally invasive surgery for the treatment of cancer has not been employed. Of course, other kinds of minimally invasive techniques such as chemotherapy and radiation treatment are widely practiced. However, these techniques have substantial debilitating side effects. Patients must suffer significantly in virtually every case.

Nevertheless, minimally invasive techniques are the future of medicine. Patient trauma and hospitalization time are reduced. In addition, costs and expenses are decreased.

OBJECTS OF THE INVENTION

An object of the present invention is to provide a medical treatment method and/or an associated apparatus.

A more particular object of the present invention is to provide a method for treating cancer.

An associated particular object of the present invention is to provide a method for destroying tumors.

It is an even more specific object of the present invention to provide a method for destroying tumors which is less invasive than conventional open-incision surgical techniques.

A further object of the present invention is to provide a cancer treatment technique which is less detrimental to the patient than other types of medical treatments in at least some respects.

These and other objects of the present invention will be apparent from the drawings and descriptions herein.

SUMMARY OF THE INVENTION

A method for treating cancer comprises, in accordance with the present invention (a) generating a series of investigatory pressure waves of respective different preselected frequencies in a patient so that the pressure waves are transmitted to a tumor through overlying tissues, (b) during this pressure wave generation, monitoring responsive oscillatory motion of the tumor and at least some internal tissues of the patient proximate to the tumor. The responsive oscillatory motion of the internal tissues of the patient arise as a result of the transmission of the pressure waves into the patient. The method also comprises (c) determining, from the responsive oscillatory motion of the tumor and the internal tissues, a pressure wave frequency which results in a resonant loading of the tumor and essentially leaves the internal tissues undamaged, and (d) generating, in the patient, treatment pressure waves of the determined pressure wave frequency and of an effective amplitude so that the tumor resonates with sufficient energy to mechanically destroy the tumor.

The resonant loading principle utilized by the present invention relies in part on the recognition that tumorous growths have characteristic resonance frequencies depending on the densities of the tumors as well as on their sizes and shapes. The present invention is directed to providing a method and an associated apparatus for testing a tumor to determine a resonant frequency or frequencies thereof and for subsequently injecting wave energy into the tumor at the resonant frequency or frequencies, to effectively tear the tumor apart.

In accordance with another feature of the present invention, the method utilizes a substrate carrying a plurality of electromechanical (e.g., piezoelectric) transducers. The generating of the investigatory pressure waves then includes placing the substrate in contact with an external surface of the patient so that the transducers are in pressure-wave-transmitting contact with an external skin surface of the patient and further includes energizing the transducers with periodic voltages of the different preselected frequencies. The energizing of the transducers includes energizing each of the transducers with voltages of a plurality of different frequencies, while the monitoring of responsive oscillatory motion of the tumor and at least some internal tissues of the patient proximate to the tumor includes monitoring responsive oscillatory motion of the tumor and the internal tissues proximate to the tumor for each of the transducers and each of the frequencies with which the respective transducers are energized.

In a preferred embodiment of the apparatus used with the method, the transducer-carrying substrate is a flexible web which conforms to the patient and thus facilitates effective contact between the multiple transducers and the skin of the patient. More specifically, where the patient has skin surfaces in different planes, the placing of the substrate in contact with an external surface of the patient includes positioning at least one of the transducers in pressure-wave transmitting contact with each of the skin surfaces.

The placement of the transducers in pressure-wave-transmitting contact with multiple skin surfaces enables the transmission of wave fronts at different angles into the patient. This capability is advantageous insofar as a target tumor may have different resonant frequencies depending on the direction of energy transmission into the tumor. In some cases, a tumor may have several resonant frequencies for respective angles or directions of wave transmission. It is possible to utilize two or more resonant frequencies simultaneously to optimally load a tumor or other undesirable internal tissue structure.

In accordance with a further feature of the present invention, the generating of the treatment pressure waves includes energizing at least one of the transducers with a periodic voltage of the pressure wave frequency or frequencies which are determined to be a resonant frequency or frequencies for the target tumor.

The monitoring of internal tissue motion in response to the excitation waves is possibly implemented by sensing pressure waves generated at a skin surface of the patient in response to motion of the tumor and the internal tissues. The pressure waves are processed by a computer to determine the responsive oscillatory motion of the tumor. This procedure is based on the realization that oscillations produced at the skin of the patient owing to internal resonant loading of internal tissues will be different from skin oscillations resulting from non-resonant motion of the internal tissues. The processing of the pressure waves optionally includes analyzing the pressure waves to determine three-dimensional shapes of internal tissue structures including the tumor and to determine modes and magnitudes of motions of the internal tissues structures.

In an alternative technique, the motion of the tumor and the internal tissues is monitored by utilizing a multiplicity of probes each having integral sensors for determining motion of a respective distal probe tip. The probes are inserted into the patient so that distal end portions of the probes are located adjacent to or near surfaces or boundaries of internal tissue structures including the tumor. Signal outputs of the sensors are then monitored to determine motion of the surfaces or boundaries of the internal tissue structures.

In yet another alternative technique for monitoring resonance behavior of internal tissue structures, the shapes and sizes of the internal tissue structures are monitored using ultrasonic pressure waves. Thus, there are two systems operating simultaneously and two sets of pressure waves passing through the patient simultaneously. One system and the pressure waves produced thereby perform the monitoring function, while the other system and the pressure waves produced thereby execute the resonant loading of target internal tissue structures. The two systems may share some of the same components. For example, the same flexible substrate may support the transducers of the two systems. Moreover, some of the transducers may be used in performing both the loading and the monitoring functions.

Accordingly, a method for performing a medical operation comprises, in accordance with the present invention, placing a plurality of electromechanical transducers in pressure-wave-transmitting contact with a patient, energizing at least some of the transducers with an ultrasonic frequency to produce ultrasonic first pressure waves in the patient, energizing at least one of the transducers with another frequency in a range below ultrasonic to produce second pressure waves in the patient, and analyzing ultrasonic third pressure waves produced at internal tissue structures of the patient in response to the first pressure waves to determine three dimensional shapes of the tissue structures and to monitor resonant motion of the tissue structures in response to the second pressure waves.

Where the one transducer is energized in seriatim with a plurality of test frequencies in the range below ultrasonic (the other frequency being one of the test frequencies), the analyzing of the third pressure waves includes determining whether any of the test frequencies results in a resonant loading of a predetermined or preselected one of the tissue structures. In this vein, the method may further comprise energizing a plurality of the transducers in seriatim with a plurality of test frequencies in the range below ultrasonic, the analyzing of the third pressure waves including identifying which of the transducers and which of the test frequencies, if any, induce a resonant loading of the predetermined one of the tissue structures. The analyzing of the third pressure waves to monitor resonant motion of the tissue structures in response to the second pressure waves includes automatically comparing sizes and shapes of the tissue structures at a succession of different times to determine changes in sizes and shapes of the tissue structures.

The method may further comprise, upon determining that one of the test frequencies is a resonant frequency of the preselected tissue structure, energizing the transducer(s) with that resonant frequency to destroy the preselected tissue structure.

A medical treatment system comprises, in accordance with the present invention, a carrier, a plurality of electromechanical transducers mounted to the carrier, an a-c current generator operatively connected to at least some of the transducers for energizing the transducers with electrical signals of a plurality of pre-established frequencies to produce first pressure waves in the patient, and an acoustic signal processor operatively connected to at least some of the transducers programmed to analyze incoming pressure waves to determine mechanical resonant characteristics of internal tissue structures of a patient, the incoming pressure waves being generated by the internal tissue structures in response to the first pressure waves, the processor being programmed more particularly to determine which of the transducers is to be energized with which of the frequencies to resonantly overload a preselected one of the tissue structures, thereby mechanically destroying the preselected or target tissue structure.

Pursuant to another aspect of the present invention, componentry is operatively connected to the processor for identifying the preselected tissue structure. This componentry includes at least one electroacoustic transducer mounted to the carrier for producing primary ultrasonic pressure waves in the patient, at least one acoustoelectric transducer mounted to the carrier for sensing secondary ultrasonic pressure waves produced at the internal tissue structures in response to the primary pressure waves, and an ultrasonic wave analyzer operatively connected to the acoustoelectric transducer for determining three-dimensional shapes of the internal tissue structures of the patient by analyzing signals generated by the acoustoelectric transducer in response to the secondary pressure waves.

The electroacoustic transducer and the acoustoelectric transducer may be taken from among the electromechanical transducers. In addition, the carrier may include a flexible web conformable to the patient. A video monitor may be linked to the analyzer for displaying an image of the internal tissue structures.

A method for treating cancer in accordance with the present invention serves to destroy tumors and is less invasive than conventional open-incision surgical techniques. The method is easy to administer, and is substantially less toxic and debilitating to patients than other techniques.

BRIEF DESCRIPTION OF THE DRAWINGS

FIG. 18 is a schematic perspective view of an ultrasonographic device in accordance with the present invention.

FIG. 19 is a schematic perspective view of another ultrasonographic device in accordance with the present invention.

FIG. 20 is a schematic perspective view of the ultrasonographic device of FIG. 19, showing the device in use on a patient.

DESCRIPTION OF THE PREFERRED EMBODIMENTS

Figure 1:
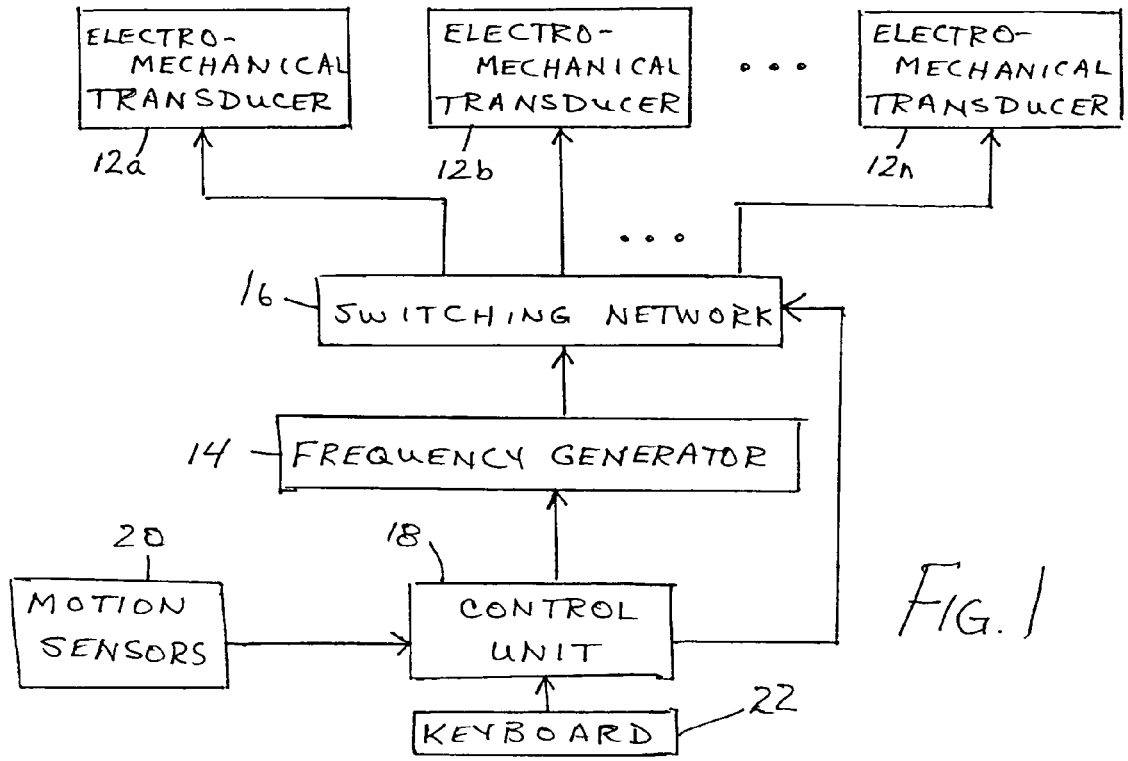
FIG. 1 is a block diagram of a system for inducing destruction of internal tissue structures of a patient by resonance loading, in accordance with the present invention.

As illustrated in FIG. 1, an apparatus for treating cancer comprises a plurality of electromechanical transducers 12a, 12b, ... 12n which are disposable in pressure-wave-transmitting contact with a patient for purposes in part of generating a series of investigatory pressure waves of respective different preselected frequencies in the patient so that the pressure waves are transmitted to a tumor through overlying tissues. Transducers 12a, 12b, ... 12n may take the form of piezoelectric crystals, electromagnets with movable cores, pneumatically actuated pistons, etc. One or more of transducers 12a, 12b, ... 12n are energized or activated with the preselected frequencies which are produced by a generator 14 and directed to the various transducers 12a, 12b ... 12n via a switching network 16 responsive to a control unit 18. During the generation of pressure waves in the patient, responsive oscillatory motion of the tumor and other internal tissue structures of the patient are monitored by control unit 18. To that end, control unit 18 receives motion information from sensors 20 positioned in effective or operative contact with the patient. The responsive oscillatory motion of the tumor and possibly other internal tissue structures of the patient arise as a result of the transmission of the pressure waves into the patient.

Control unit 18 determines, from the responsive oscillatory motion of the tumor and the other internal tissues, at least one pressure wave frequency which results in a resonant loading of the tumor and essentially leaves the other (normal) internal tissues undamaged. Control unit 18 concomitantly determines which transducer 12a, 12b, ... or 12n is to be used to generate the resonant frequency to destroy the tumor.

Thus, control unit 18 first executes a testing procedure to determine the effects of various pressure wave frequencies on a target tumor as well as on normal internal tissue structure of the patient. This testing procedure is generally carried out for several, if not all, transducers 12a, 12b, ... 12n. In a subsequent treatment procedure, control unit 18 generates, in the patient, treatment pressure waves of one or more resonant frequencies and of effective amplitudes so that the tumor resonates with sufficient energy to be mechanically destroyed. The fragmentation of a tumor by resonant loading contemplates the tearing apart of various components of the tumor, including the blood supply, and even individual cells. Suction instruments (not shown) may be inserted into the patient via minimally invasive techniques, e.g., laparoscopically, to remove the tumor fragments. However, removal is considered in most cases to be unnecessary.

The test frequencies may be limited to a range which is predetermined in accordance with well known laws of wave propagation. The range of test frequencies will depend in part on the density of the target tumor as well as on its size and shape. Control unit 18 may be instructed via a keyboard 22 to limit the test frequencies to a particular range in accordance with these considerations. Alternatively, control unit 18 may be programmed to automatically determine a range of test frequencies upon being provided with information as to the size and shape of a target tissue structure, and optionally as to the density of the target.

Figure 2:
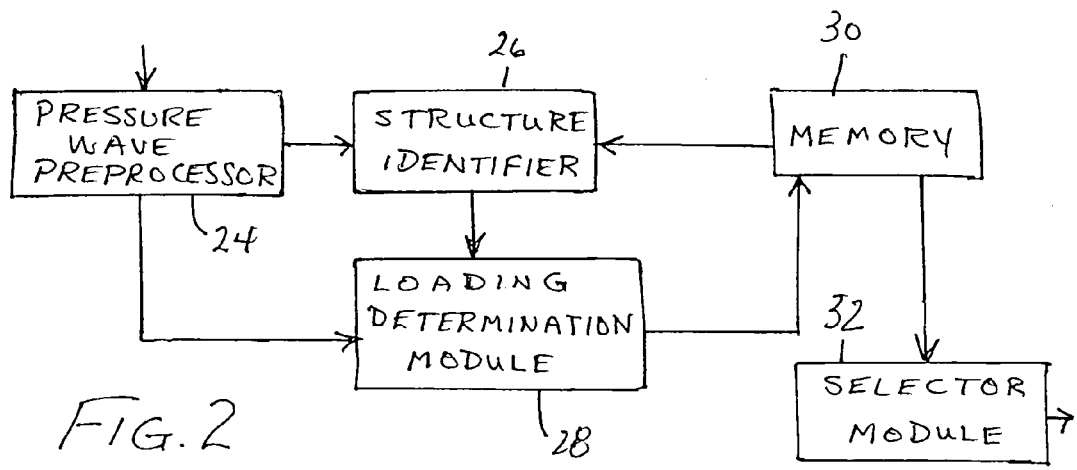
FIG. 2 is a block diagram of selected modules of a control unit illustrated in FIG. 1.

As illustrated in FIG. 2, control unit 18 may include a pressure wave preprocessor 24. Pressure wave preprocessor 24 is connected at an input to sensors 20 (FIG. 1) and at outputs to a structure identifier 26 and a loading determination module 28. Identifier 26 uses pattern recognition techniques, comparing incoming pressure wave information with data preloaded into a memory 30, and cooperates with loading determination module 28 to determine which internal tissue structures of the patient are exhibiting what degrees of resonant loading in response to the various test frequencies with which the various transducers 12a, 12b, ... 12n are energized by frequency generator 14. The results of the testing stage of operation of control unit 18 are temporarily stored in memory 30 and subsequently accessed by a selector module 32. Module 32 determines which transducer or transducers 12a, 12b, ... 12n and which test frequency or frequencies are to be used in the treatment stage to destroy a preselected target structure such as a tumor.

Generally, control unit 18 is a microprocessor wherein the functional blocks of FIG. 2 are implemented by generic digital processing circuits as modified by programming.

Motion sensors 20 may take the form of electromechanical transducers similar to transducers 12a, 12b, . . . 12n. Generally, the exact locations of transducers 12a, 12b, . . . 12n and even of sensors 20 are not critical to carrying out a tumor destruction treatment. It is only necessary that the reaction of a target tissue structure to pressure waves of different frequencies can be ascertained. Nevertheless, the processing of pressure waves arriving at the skin surface of the patient owing to induced oscillations of internal tissue structures optionally includes analyzing those arriving pressure waves to determine three-dimensional shapes of internal tissue structures including the tumor and to determine modes and magnitudes of motions of the internal tissues structures.

Figure 3:
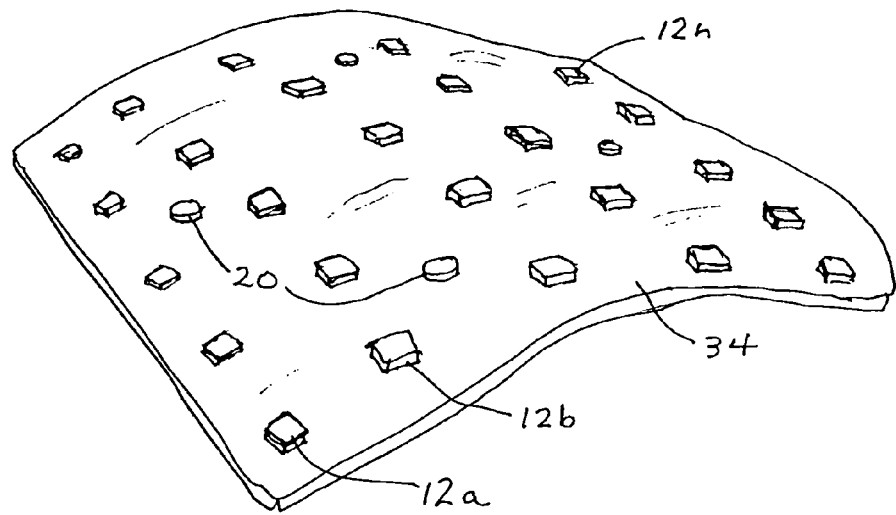
FIG. 3 is a schematic perspective view showing a particular embodiment of the system of FIG. 1.

As illustrated in FIG. 3, transducers 12a, 12b, . . . 12n and sensors 20 may be attached to a flexible substrate or web 34. Transducers 12a, 12b, . . . 12n and sensors 20 are placed in pressure-wave transmitting contact with an external surface of the patient by draping or wrapping the flexible web 34 on or around the patient. Web 34 conforms to the patient and thus facilitates effective contact between the multiple transducers 12a, 12b, . . . 12n and sensors 20, on the one hand, and the skin of the patient, on the other hand. More specifically, where the patient has skin surfaces in different planes, the placing of web 34 in contact with an external surface of the patient includes positioning at least one transducer 12a, 12b, . . . 12n in pressure-wave transmitting contact with each of the skin surfaces.

The placement of transducers 12a, 12b, . . . 12n in pressure-wave-transmitting contact with multiple skin surfaces enables the transmission of wave fronts at different angles into the patient. This capability is advantageous insofar as a target tumor may have different resonant frequencies depending on the direction of energy transmission into the tumor. In some cases, a tumor may have several resonant frequencies for respective angles or directions of wave transmission. It is possible to utilize two or more resonant frequencies simultaneously to optimally load a tumor or other undesirable internal tissue structure.

Figure 4:
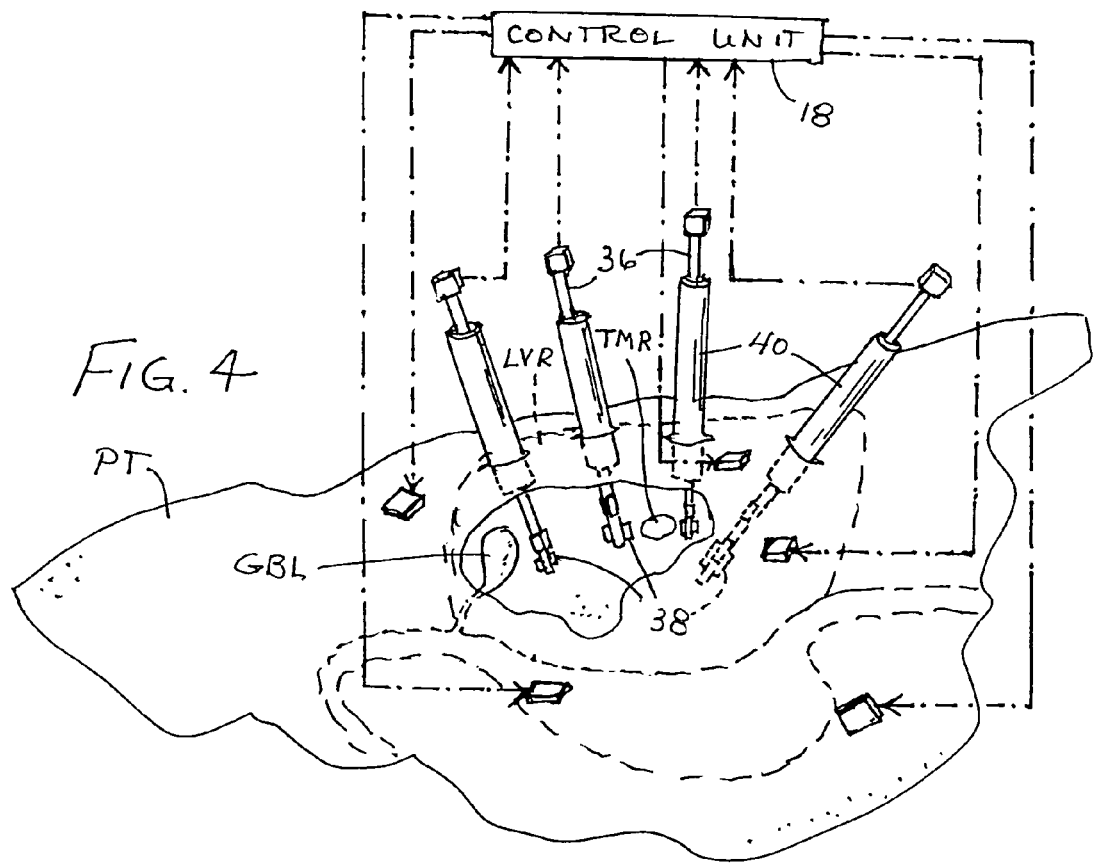
FIG. 4 is partially a schematic perspective view and partially a block diagram showing another particular embodiment of the system of FIG. 1.

In an alternative technique illustrated in FIG. 4, the motions of a target tissue structure such as a tumor TMR and other internal tissues such as a liver LVR and gall bladder GBL are monitored by utilizing a multiplicity of probes 36 each provided along a respective distal end portion (not separately designated) with one or more sensors 38 for determining motion of tissues located near the distal end portions. The distal end portions of probes 36 are inserted through cannulas 40 into a patient PT so that the distal end portions of the probes are located adjacent to surfaces or boundaries of internal tissue structures including the tumor TMR. Signal outputs of sensors 38 are then monitored to determine motion of the surfaces or boundaries of the internal tissue structures. Sensors 38 perform the function of sensors 20 in FIG. 1.

In yet another alternative technique for monitoring resonance behavior of internal tissue structures, the shapes and sizes of the internal tissue structures are monitored using ultrasonic pressure waves. In carrying out this technique, two systems are used which operate simultaneously to generate two sets of pressure waves in the patient. One system and the pressure waves produced thereby perform the monitoring function, while the other system and the pressure waves produced thereby execute the resonant loading of target internal tissue structures. The two systems may share some of the same components. For example, the same flexible substrate may support the transducers of the two systems. Moreover, some of the transducers may be used in performing both the loading and the monitoring functions.

The ultrasonic imaging systems discussed below may be used to generate visually perceptible images of a target tumor on a video monitor. This image may be viewed by an operator to monitor resonance loading of the tumor. It is generally contemplated that the computer generating the images of the internal tissue structures of a patient from ultrasonic scanning of those internal tissues will also automatically and continuously calculate the dimensions of the internal tissue structures during the transmission of relatively low frequency pressure waves into the patient, in order to determine one or more resonance frequencies of a target structure such as a tumor. Generally, the test frequencies and the ultimately determined resonance frequency or frequencies are in a range lower than ultrasonic.

Figure 5:
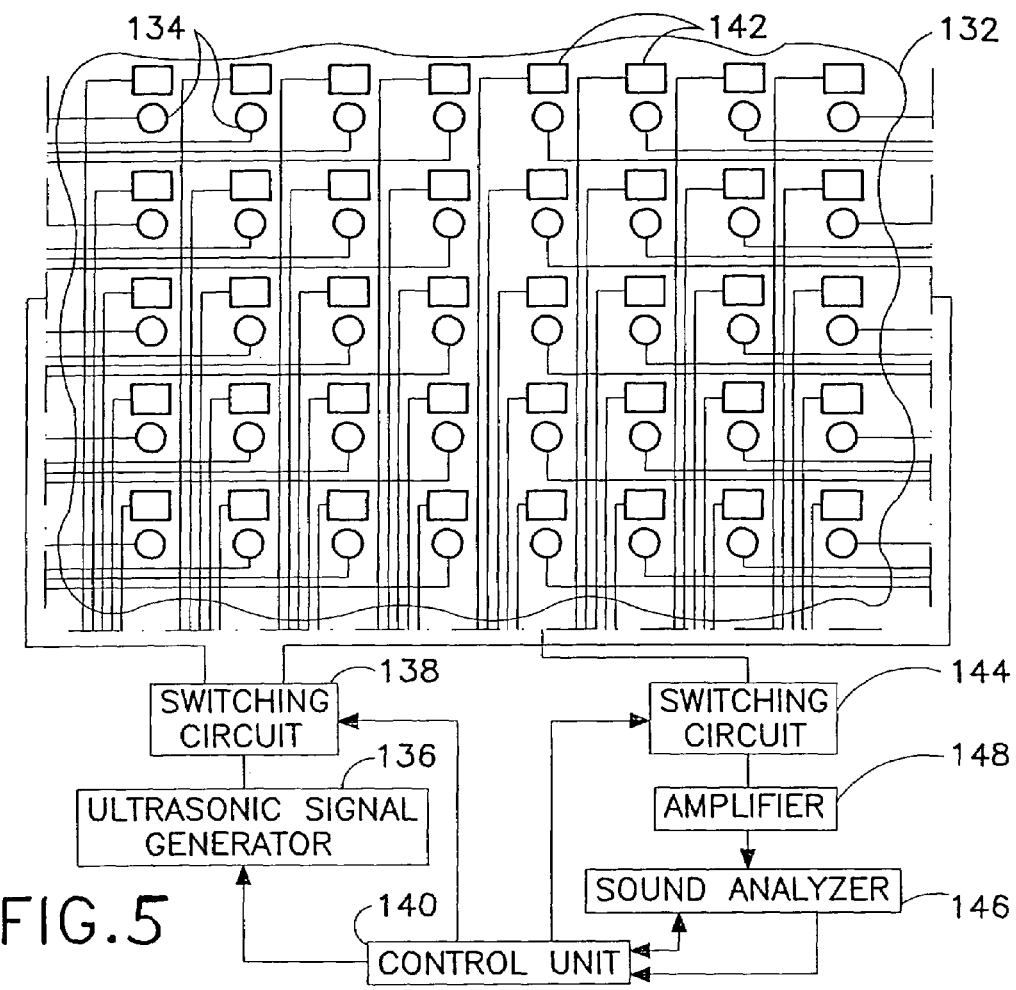
FIG. 5 is a diagram of an ultrasonography device utilizable in a resonance treatment method n accordance with the present invention.

FIG. 5 shows an ultrasonographic image generating apparatus which may be used to automatically monitor internal tissue structures of a patient during a testing stage of a resonance treatment procedure as discussed above. A flexible web 132 carries a plurality of piezoelectric electroacoustic transducers 134 in a substantially rectangular array. Transducers 134 are each connectable to an ultrasonic signal generator 136 via a switching circuit 138. Switching circuit 138 is operated by a control unit 140 to connect transducers 134 to signal generator 136 in a predetermined sequence, depending on the area of a patient's body which is being ultrasonically scanned.

Web 132 also carries a multiplicity of acoustoelectric transducers or sensors 142 also arranged in a substantially rectangular array. Sensors 142 are connected to a switching circuit 144 also operated by control unit 140. An output of switching circuit 144 is connected to a sound or pressure wave analyzer 146 via an amplifier 148.

Web 132 is draped over or placed around a portion of a patient's body which is to be monitored ultrasonically. Control unit 140 then energizes signal generator 136 and operates switching circuit 138 to activate transducers 134 in a predetermined sequence. Depending on the transducer or combination of transducers 134 which are activated, control unit 140 operates switching circuit 144 to connect a predetermined sequence of sensors 142 to pressure wave analyzer 146. Pressure wave analyzer 146 and control unit 140 cofunction to determine three dimensional structural shapes from the echoes detected by sensors 142.

Control unit 140 is connected to ultrasonic signal generator 136 for varying the frequency of the generated signal.

Figure 6:
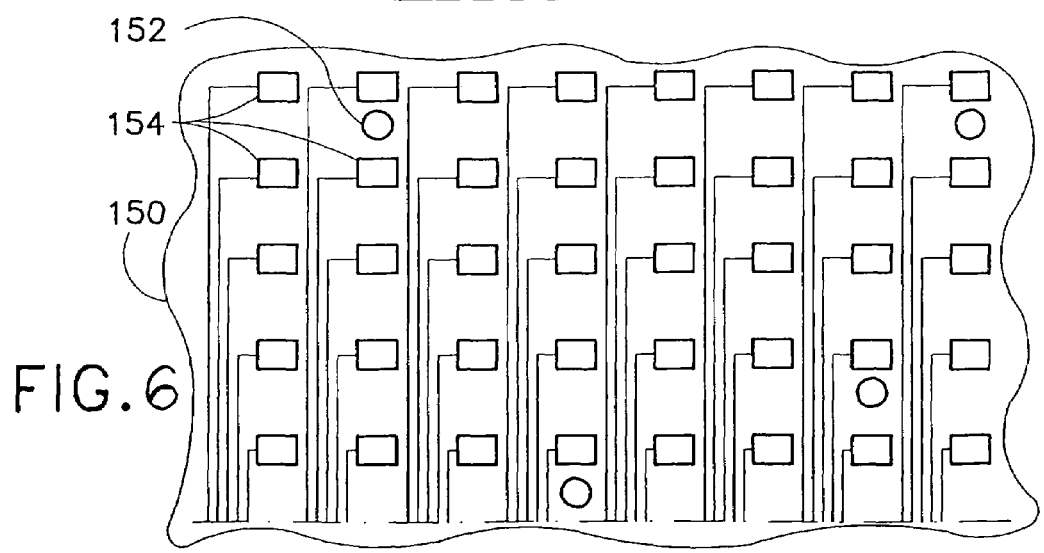
FIG. 6 is a diagram showing a modification of the device of FIG. 5.

FIG. 6 shows a modified ultrasonography web 150 having a limited number of electroacoustic transducers 152 and generally the same number and disposition of sensors 154 as in web 132.

Web 132 or 150 may be substantially smaller than illustrated and may correspondingly carry reduced numbers of transducers 134 and 152 and sensors 142 and 154. Specifically, web 132 or 150, instead of being a sheet large enough to wrap around a torso or arm of a patient, may take a strip-like form which is periodically moved during use to different, predetermined, locations on the patient. Control unit 140 and pressure wave analyzer 146 are programmed to detect internal organic structures from the data obtained at the different locations that the web 132 or 150 is juxtaposed to the patient.

Web 132 or 150 may include additional transducers (not illustrated) for emitting lower-frequency pressure waves into the patient to implement the resonance testing and treatment procedures discussed above. Alternatively, it is possible to generate the lower-frequency pressure waves using electroacoustic transducers 134 and 152. Sound analyzer 146 and control unit 140 are programmed to carry out the resonance testing and treatment procedures.

Figure 7:
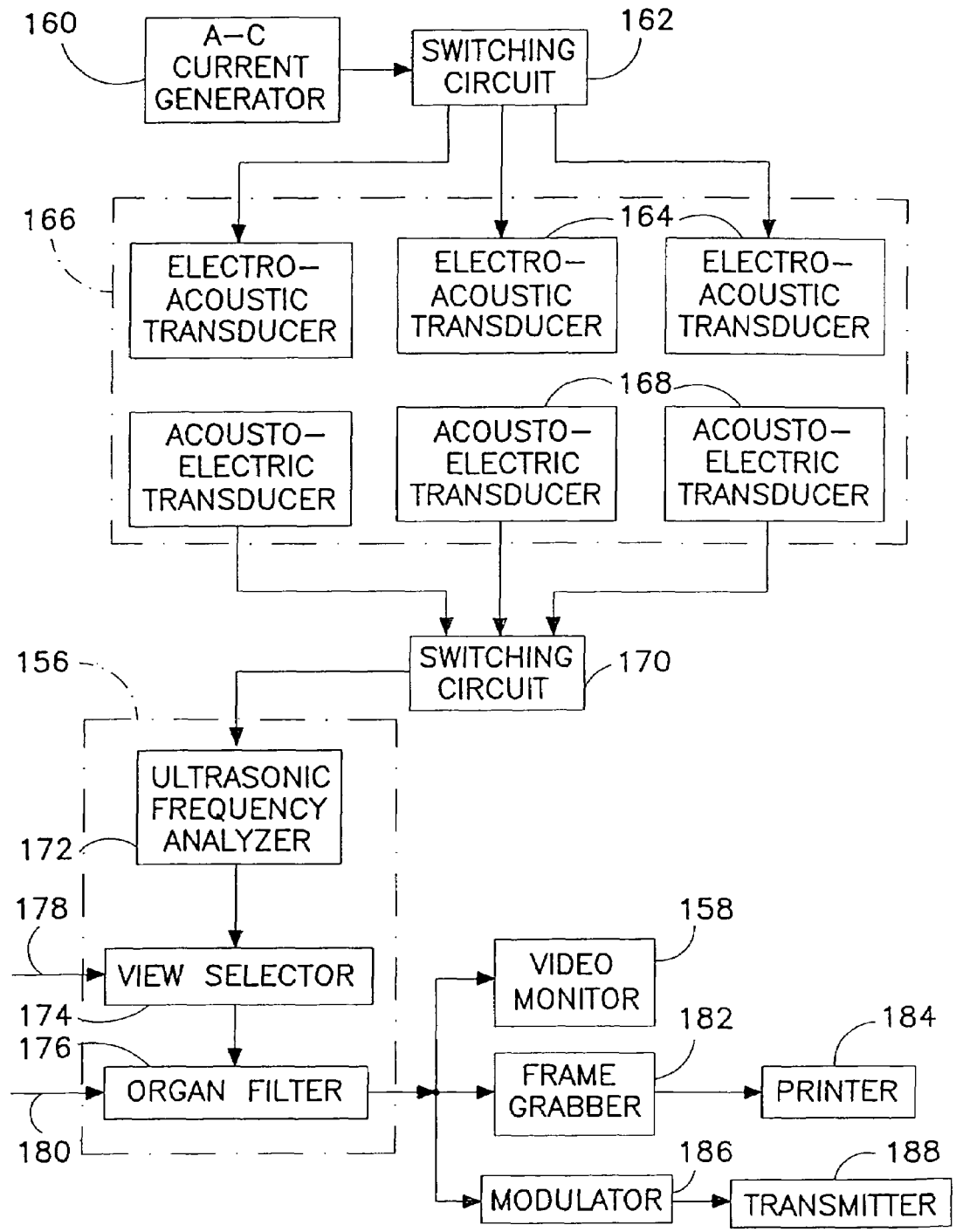
FIG. 7 is a block diagram of an ultrasonographic imaging apparatus similar to the device of FIGS. 5 and 6, for use in diagnostic and therapeutic procedures particularly utilizing mechanical resonance in accordance with the present invention.

FIG. 7 illustrates a modification of the ultrasonography apparatus of FIGS. 5 and 6 which is employable in diagnostic or therapeutic operations involving the insertion of an instrument into a patient, for example, a suction instrument for removing a tumor fragmented by resonant loading as described above. A control unit 156 for performing operations of control unit 140 is connected at an output to a video monitor 158. As discussed hereinafter with reference to FIGS. 9 and 10, a diagnostician, surgeon or other medical specialist inserts a distal end of a medical instrument into a patient in response to video feedback provided by the ultrasonography apparatus including video monitor 158.

Figure 10:
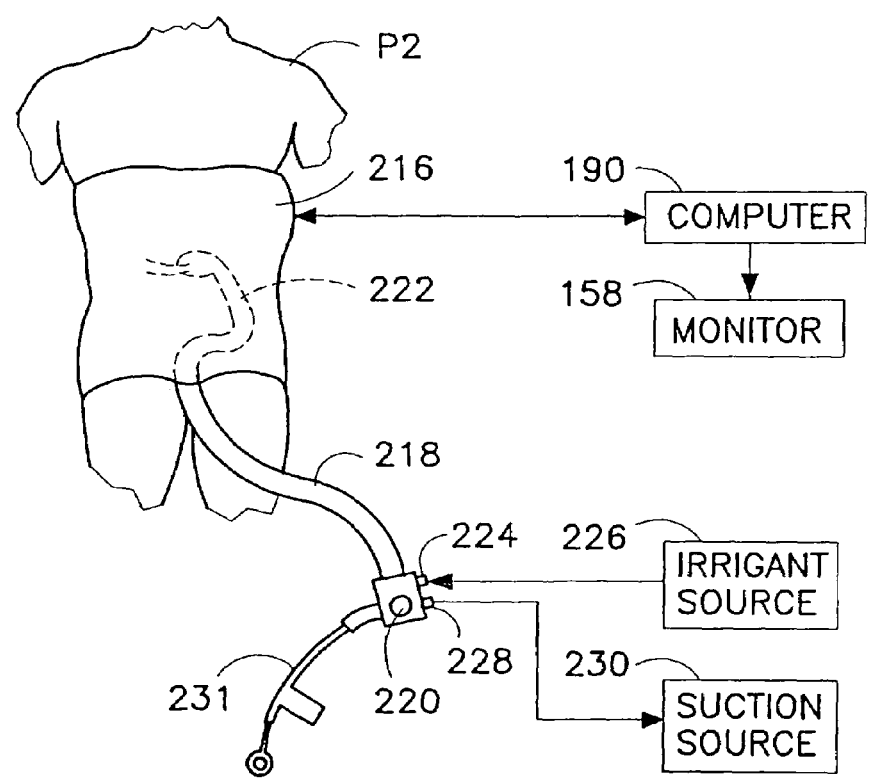
FIG. 10 is a partial schematic perspective view including a block diagram showing use of an ultrasonographic imaging device in another minimally invasive diagnostic or therapeutic procedure.

As further illustrated in FIG. 10, an a-c current or ultrasonic signal generator 160 is connected via a switching circuit 162 to different piezoelectric type electroacoustic transducers 164 in seriatim. Transducers 162 are mounted in interspaced fashion to a flexible web 166 which also carries an array of spaced piezoelectric type acoustoelectric transducers 168.

A flexible web carrying electromechanical transducers is placed adjacent to a skin surface of a patient. In some cases, it may be beneficial to provide a layer of fluid between the skin surface of the patient and the web 166 to facilitate ultrasonic wave transmission from web 166 to the patient and from the patient back to the web. In response to the periodic energization of transducers 162, ultrasonic pressure waves are reflected from internal organic structures of the patient and sensed by acoustoelectric transducers 168. Electrical signals generated by transducers 168 in response to the reflected pressure waves are fed via a switching circuit 170 to control unit 156.

As discussed hereinabove with reference to control unit 140 in FIG. 5, control unit 156 controls switching circuits 162 and 170 to energize emitting transducers 164 in a predetermined sequence and to selectively couple receiving transducers 168 in a pre-established sequence to a pressure wave or ultrasonic frequency analyzer 172 in control unit 156. The sequencing depends on the portion of the patient being monitored.

In addition to pressure wave or ultrasonic frequency analyzer 172, control unit 156 includes a view selector 174 and a filter stage 176. View selector 174 is operatively connected at an input to analyzer 172 and at an output to video monitor 158 for selecting an image for display from among a multiplicity of possible images of the internal organs detected by analyzer 172. View selector 174 may be provided with an input 178 from a keyboard (not shown) or other operator interface device for enabling an operator to select a desired view. For example, during the insertion of a suction instrument into the patient or during manipulation of that instrument to remove a fragmented tumor from the patient, the medical practitioner may sequentially select views from different angles to optimize the practitioner's perception of the spatial relation between the distal tip of the instrument and the patient's internal organs.

Filter stage 176 is operatively connected to analyzer 172 and video monitor 158 for optionally eliminating a selected organ from the displayed image. Filter stage 176 is provided with an input 180 from a keyboard (not shown) or other operator interface device for enabling an operator to select an organ for deletion from the displayed image. This facilitates the viewing of a tumor by enabling the selective removal of overlying tissues in the image viewed on monitor 158.

Filter stage 176 may also function to highlight selected organs or target tissue structures such as a tumor. The pattern recognition techniques discussed above are used to detect selected structures. The highlighting may be implemented exemplarily through color, intensity, cross-hatching, or outlines.

As further illustrated in FIG. 7, control unit 156 is optionally connected at an output to a frame grabber 182 for selecting a particular image for reproduction in a fixed hard copy via a printer 184. In addition, ultrasonically derived real-time image information may be encoded by a modulator 186 onto a carrier wave sent to a remote location via a wireless transmitter 188. Selected images for printing or long-range transmission may include images of a target treatment site before and after resonance therapy as described above with reference to FIGS. 1 and 2.

Figure 8:
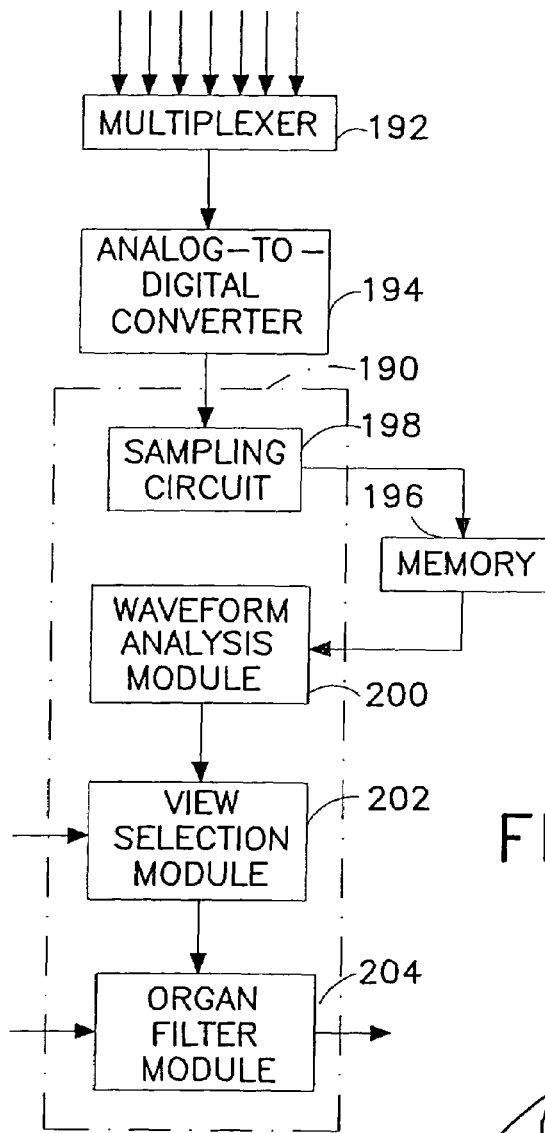
FIG. 8 is a block diagram showing a modification of the apparatus illustrated in FIG. 7.

FIG. 8 depicts the ultrasonography apparatus of FIG. 7 in a form wherein control unit 156 (FIG. 7) is realized as a specially programmed general purpose digital computer 190. A switching circuit or multiplexer 192 relays signals incoming from respective acoustoelectric transducers 168 (FIG. 7) in a predetermined intercalated sequence to an analog-to-digital converter 194, the output of which is stored in a computer memory 196 by a sampling circuit 198 of computer 190. A wave analysis module 200 of computer 190 retrieves the digital data from memory 196 and processes the data to determine three dimensional organic structures inside a patient. This three-dimensional structural data is provided to a view selection module 202 for deriving two-dimensional images for display on monitor 158 (FIG. 10). A filter module 204 is provided for removing selected organs from the image presented on the visual display or video monitor 158. Sampling circuit 198, wave analysis module 200, view selection module 202, and filter module 204 are program-modified generic digital circuits of computer 190.

Figure 9:
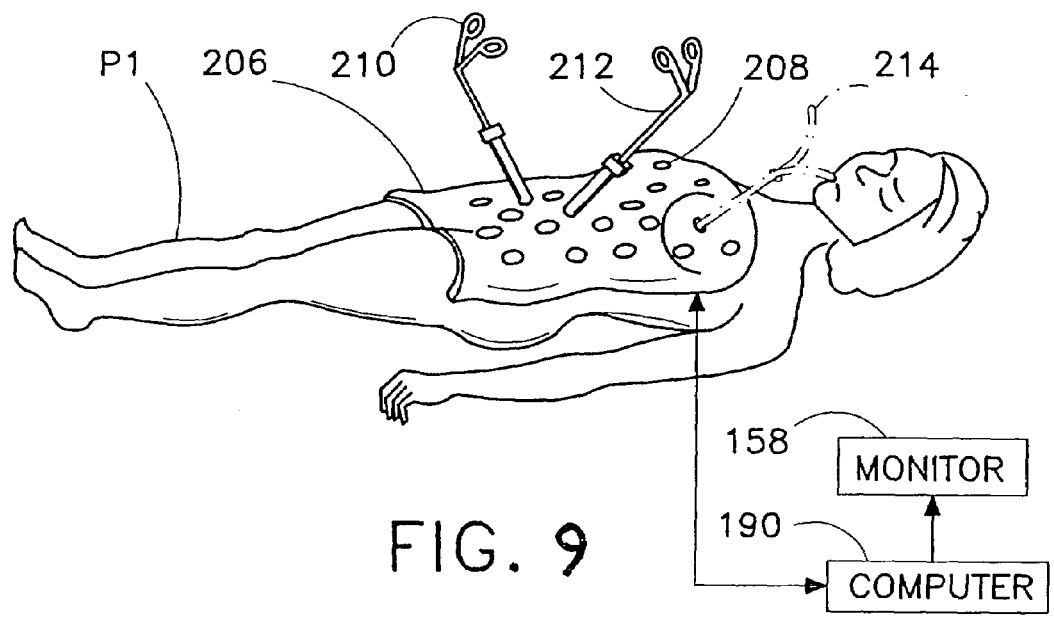
FIG. 9 is partially a schematic perspective view and partially a block diagram showing use of an ultrasonographic imaging device in a minimally invasive diagnostic or therapeutic procedure.

FIG. 9 shows a use of a flexible ultrasonic sensor web 206 which may be any of the flexible ultrasonic sensor webs described herein, except that web 206 is additionally provided with a plurality of apertures or perforations 208. Web 206 carries ultrasonic transmitters and receivers as well as transducers 12*a*, 12*b*, . . . 12*n* (FIGS. 1 and 3) for the production of resonance-frequency pressure waves in a patient P1. After the placement of web 206 in pressure-wave transmitting contact with a skin surface of patient P1, elongate diagnostic or therapeutic instruments such as laparoscopic surgical instruments 210 and 212, suction devices, and possibly motion sensing probes 36 (FIG. 4) are inserted through respective openings 208 in web 206 to perform a surgical or diagnostic operation on a preselected internal tissue structure of patient P1. This operation is effectuated by viewing a real time image of the distal ends of the instruments 210 and 212 in relation to the patient's internal organic structures as determined by control unit 156 or computer 190. Generally, the image on monitor 158 is viewed during insertion of instruments 210 and 212 to enable a proper employment of those instruments. Also, the video images on monitor 158 are viewed to enable a proper carrying out of the "laparoscopic" surgical operation on the designated internal organ of the patient P1. Strictly speaking, this operation is not a laparoscopic operation, since a laparoscope is not used to provide a continuing image of the patient's internal organic structures and the distal ends of instruments 210 and 212.

There are multiple advantages to using sonographic web 206 instead of a laparoscope. Fewer perforations need be made in the patient for the same number of surgical instruments. In addition, multiple views of the patient's internal organic structures are possible, rather than a single view through a laparoscope. Generally, these multiple views may differ from one another by as little as a few degrees of arc. Also, particularly if web 206 is extended essentially around patient P1, viewing angles may be from under the patient where a laparoscopic could not realistically be inserted.

Web 206 may be used to insert ancillary tubular instruments such as catheters and drainage tubes, for example, for thoracentesis and abscess drainage and other operation which may be ancillary to the destruction of a tumor. The tubes or catheters are inserted through apertures 208 under direct real time observation via monitor 158.

Web 206 may be used to effectuate additional diagnostic investigations other than resonance testing. For example, a biopsy instrument 214 may be inserted through an aperture 208 to perform a breast biopsy, a liver biopsy, a kidney biopsy, or a pleural biopsy, to obtain information on a tumor or other target tissue structure.

As illustrated in FIG. 10, a flexible ultrasonic sensor web 216, which may be any of the flexible ultrasonic sensor webs described herein, may be used in a diagnostic or therapeutic operation utilizing a flexible endoscope-like instrument 218. Instrument 218 has a steering control 220 for changing the orientation of a distal tip 222 of the instrument. Instrument 218 also has a port 224 connected to an irrigant source 226 and another port 228 connected to a suction source. In addition, instrument 218 is provided a biopsy channel (not shown) through which an elongate flexible biopsy instrument or surgical instrument 230 is inserted.

Instrument 218 is considerably simplified over a conventional endoscope in that instrument 218 does not require fiber-optic light guides for carrying light energy into a patient P2 and image information out of the patient. Instead, visualization of the internal tissues and organ structures of patient P2 is effectuated via monitor 158 and control unit 156 or computer 190. As discussed above with reference to FIG. 9, the sonographic imaging apparatus if web 216 is extended essentially around patient P2, images may be provided from multiple angles, not merely from the distal tip 222 of instrument 218. The assembly or system of FIG. 10 is useful in diagnosing and treating tumors of the colon.

View selector 174 and organ filter stage 176 or view selection module 202 and filter module 204 may function in further ways to facilitate viewing of internal organic structures. In addition to organ removal and highlighting, discussed above, a zoom capability may be provided. The zoom or magnification factor is limited only by the resolution of the imaging, which is determined in part by the frequency of the ultrasonic pressure waves.

Figure 11:
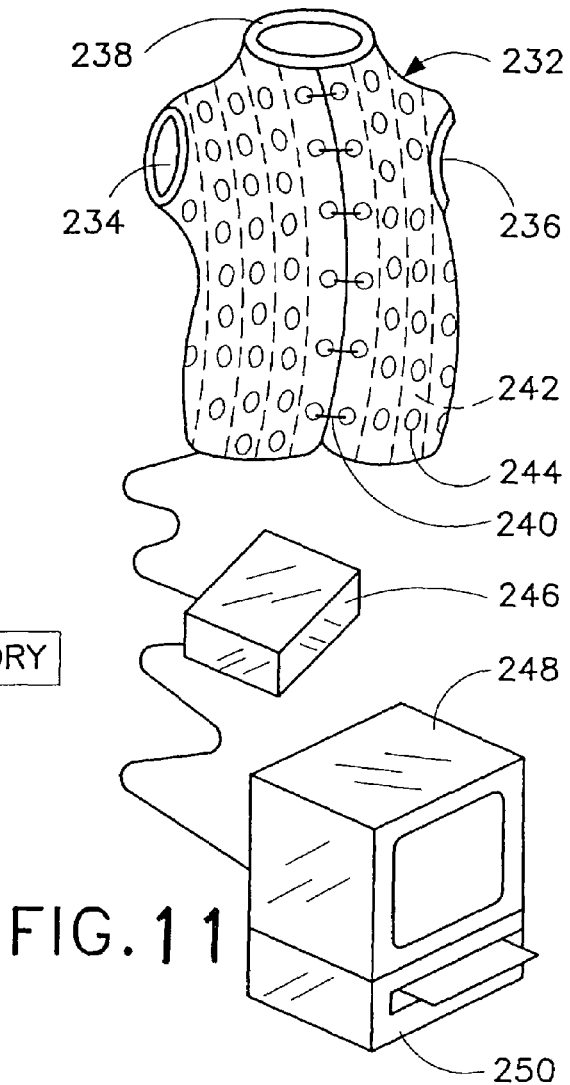
FIG. 11 is a schematic perspective view of yet another ultrasonographic imaging device which includes a sensor vest in a closed, use configuration.
Figure 12:
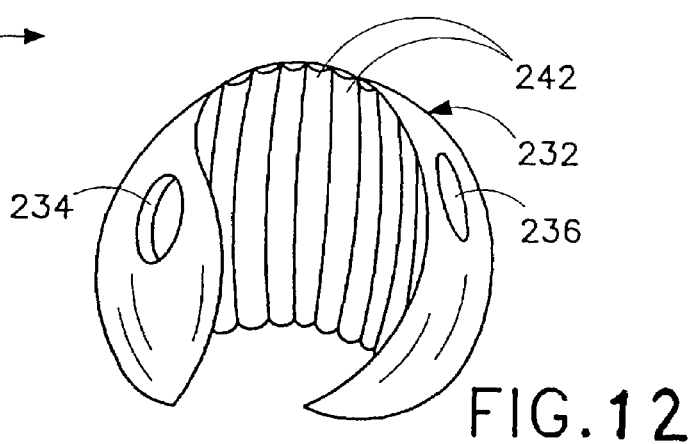
FIG. 12 is a schematic perspective view of the sensor vest of FIG. 11, showing the vest in an open configuration.

FIGS. 11 and 12 depict a specialized ultrasonic sensor web 232 in the form of a garment such as a vest. Sensor vest 232 has arm holes 234 and 236, a neck opening 238 and fasteners 240 for closing the vest about a patient. In addition, sensor vest 232 is provided with a plurality of elongate chambers 242 which receive fluid for expanding the vest into conformation with a patient's skin surface, thereby ensuring contact of the vest with a patient's skin surface and facilitating the transmission of ultrasonic pressure waves to and from ultrasonic transducers 244. FIG. 11 shows a computer 246, a video monitor 248 and a printer 250 used as described above.

Sensor vest 232 may be understood as a container assembly having fluid-filled chambers 242 with flexible inwardly facing walls (not separately designated) which conform to the patient. The surrounding of the patient, or a portion of the patient, facilitates the detection and application of resonance frequencies to a target tumor.

Figure 13:
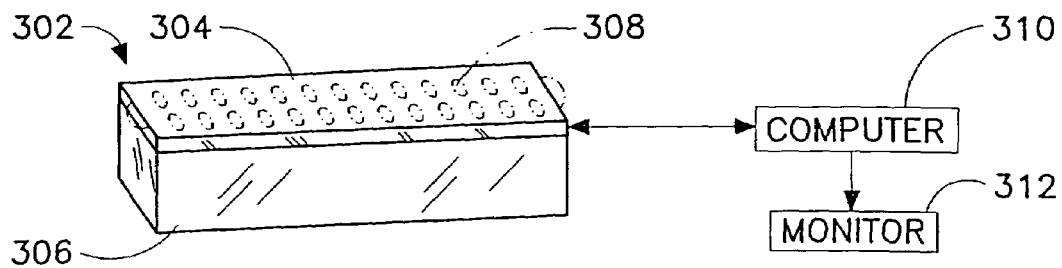
FIG. 13 is partially a schematic perspective view and partially a block diagram of an ultrasonic diagnostic imaging device.
Figure 14:
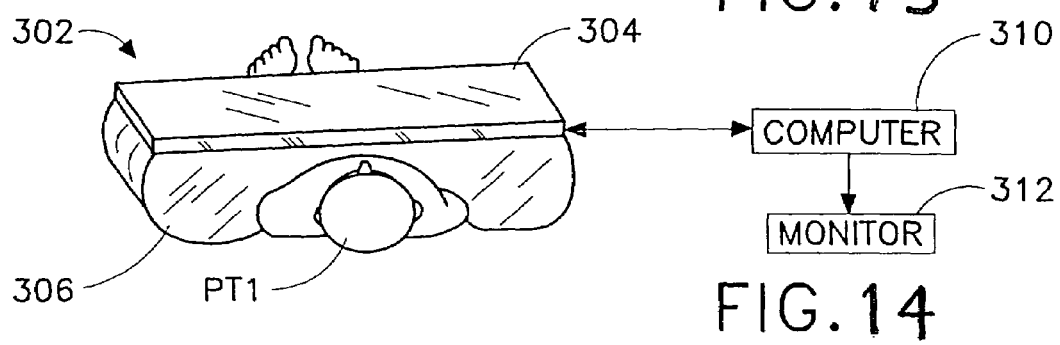
FIG. 14 is partially a schematic perspective view and partially a block diagram of the ultrasonic diagnostic imaging device of FIG. 13, showing the device in use with a patient.

As illustrated in FIG. 13, an ultrasonography apparatus comprises a container assembly 302 including a substantially rigid plate 304 attached to a flexible bladder or bag 306. Bladder or bag 306 is filled with a liquid and is sufficiently flexible to substantially conform to a patient when the container assembly 302 is placed onto a patient PT1, as illustrated in FIG. 14. A liquid may be deposited on the patient prior to the placement of container assembly 302 on patient PT1.

Plate 304 is provided with multiple ultrasonic pressure wave generators and detectors 308 as described above with respect to FIGS. 5 and 6 and FIGS. 11 and 12. Plate 308 also carries pressure-wave transducers 12a, 12b, ... 12n (FIG. 1) for resonance therapy. Alternatively, as indicated above, pressure wave generators and detectors 308 may be used to perform the testing and treatment functions of transducers 12a, 12b, ... 12n. Generators and detectors 308 are connected to a computer 310 having essentially the same functional structures and programming as computer 190 for implementing sequential generator energization and sequential detector sampling, as described above. Computer 310 also has program-modified digital processing circuits, as described above with reference to FIGS. 1 and 2, for generating test waves to detect one or more resonance frequencies of a target tissue structure and for generating treatment waves for selectively destroying the target tissue structure. Computer 310 is connected to a monitor 312 for displaying images of internal tissue structures of patient PT1. Computer 310 has the capability of alternately displaying organ images from different angles, as discussed above. FIG. 18 depicts another ultrasonography apparatus useful for both diagnostic investigations and minimally invasive surgical operations. The apparatus comprises a container assembly 314 which includes a fluid-filled sack or bag 316 for receiving a patient PT2. Sack or bag 316 include a flexible upper wall 318 which deforms to conform to the patient PT2 upon placement of the patient onto the bag. Bag 316 is supported on two or more sides by substantially rigid walls or panels 320 and 322. Panels 320 and 322 are either integral with bag 316 or separable therefrom. Panels 320 and 322, as well as an interconnecting bottom panel 324, may be provided with multiple pressure wave generators and detectors (not shown) as described above with respect to FIGS. 1, 5 and 6, FIGS. 11 and 12, and FIG. 13. These generators and detectors are connected to a computer 326 having essentially the same functional structures and programming as computer 190 for implementing sequential generator energization and sequential detector sampling, as described above. Computer 326 is connected to a monitor 328 for displaying images of internal organs of patient PT2. Computer 326 has the capability of alternately displaying organ images from different angles, as discussed above. Computer 326 also controls (a) the transmission of test frequencies into the patient for purposes of determining resonance frequencies of a tumor or other selected internal tissue structure and (b) the transmission of one or more detected resonance frequencies from one or more transducers The pressure wave generators and detectors may be provided in a separate carrier 330 disposable, for example, between bottom panel 324 and bag 316, as shown in FIG. 15.

Figure 15:
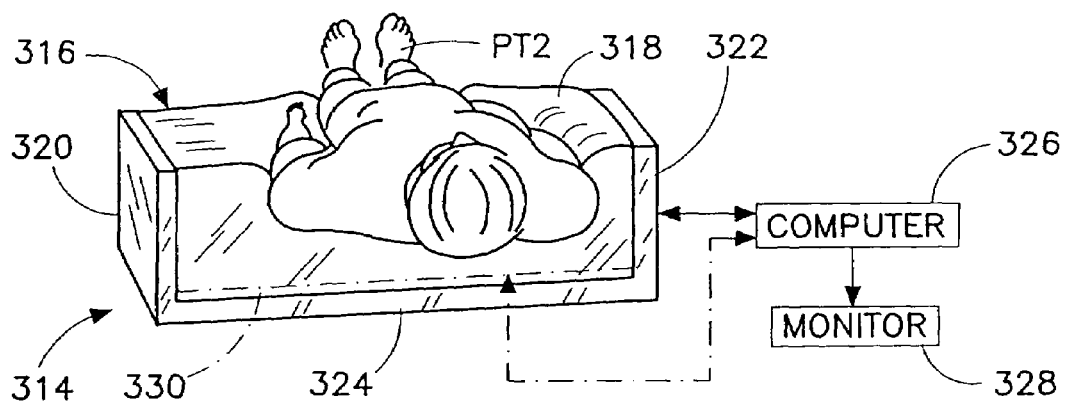
FIG. 15 is partially a schematic perspective view and partially a block diagram of another ultrasonic diagnostic imaging device, showing the device in use with a patient.
Figure 16:
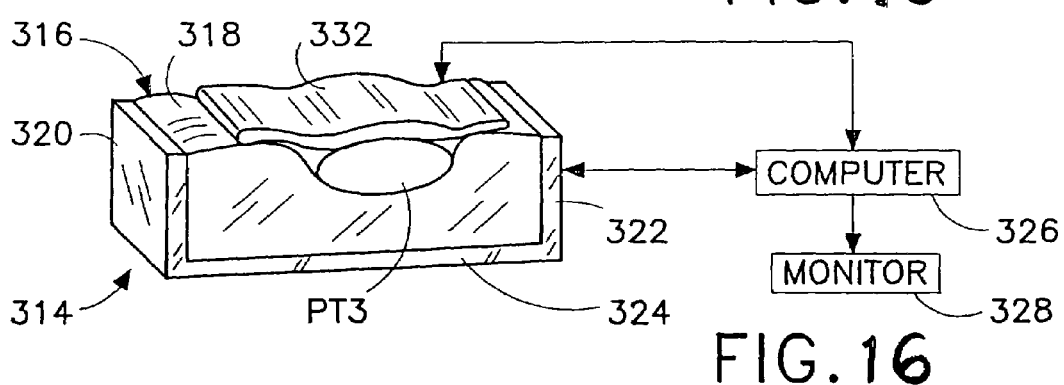
FIG. 16 is partially a schematic perspective view and partially a block diagram of the ultrasonic diagnostic imaging device of FIGS. 14 and 15, showing a modification of the device of those figures.

As illustrated in FIG. 16, the apparatus of FIG. 15 may be used in conjunction with a flexible web or cover sheet 332 identical to web 132, 150, or 206 (FIG. 5, 6, or 9). Web or cover sheet 332 is operatively connected to computer 326 for providing ultrasonically derived organ position and configuration data to the computer for displaying organ images on monitor 328. The use of web or sheet 332 enables the disposition of wave generators and detectors in a 360° arc about a patient PT3 (diagrammatically illustrated in FIG. 16), thereby facilitating image production, resonance testing and selective resonance-induced tissue destruction. Where web or sheet 332 takes the form of web 206, the sheet is provided with apertures (see FIG. 9 and associated description) for enabling the introduction of minimally invasive surgical instruments into the patient PT3.

As discussed above, contact surfaces are advantageously wetted with liquid to facilitate pressure wave transmission, particularly ultrasonic pressure wave transmission, over interfaces.

As discussed hereinafter with reference to FIG. 17, video monitor 158 (FIGS. 7, 9, and 10) or monitor 328 (FIG. 16) may take the form of a flexible video screen layer attached to web 132, 150, 166 or 206 (FIG. 5, 6, 7, 9) or web 332 (FIG. 16). This modification of the ultrasonographic imaging devices discussed above is considered to be particularly advantageous in medical diagnosis and treatment procedures. The web or substrate with the video screen is disposed on a selected body portion of a patient, for example, the abdomen (FIGS. 9 and 18) or a shoulder (FIGS. 19A, 19B) or knee (FIG. 20B), so that the substrate and the video screen layer substantially conform to the selected body portion and so that the video screen is facing away from the body portion.

Figure 17:
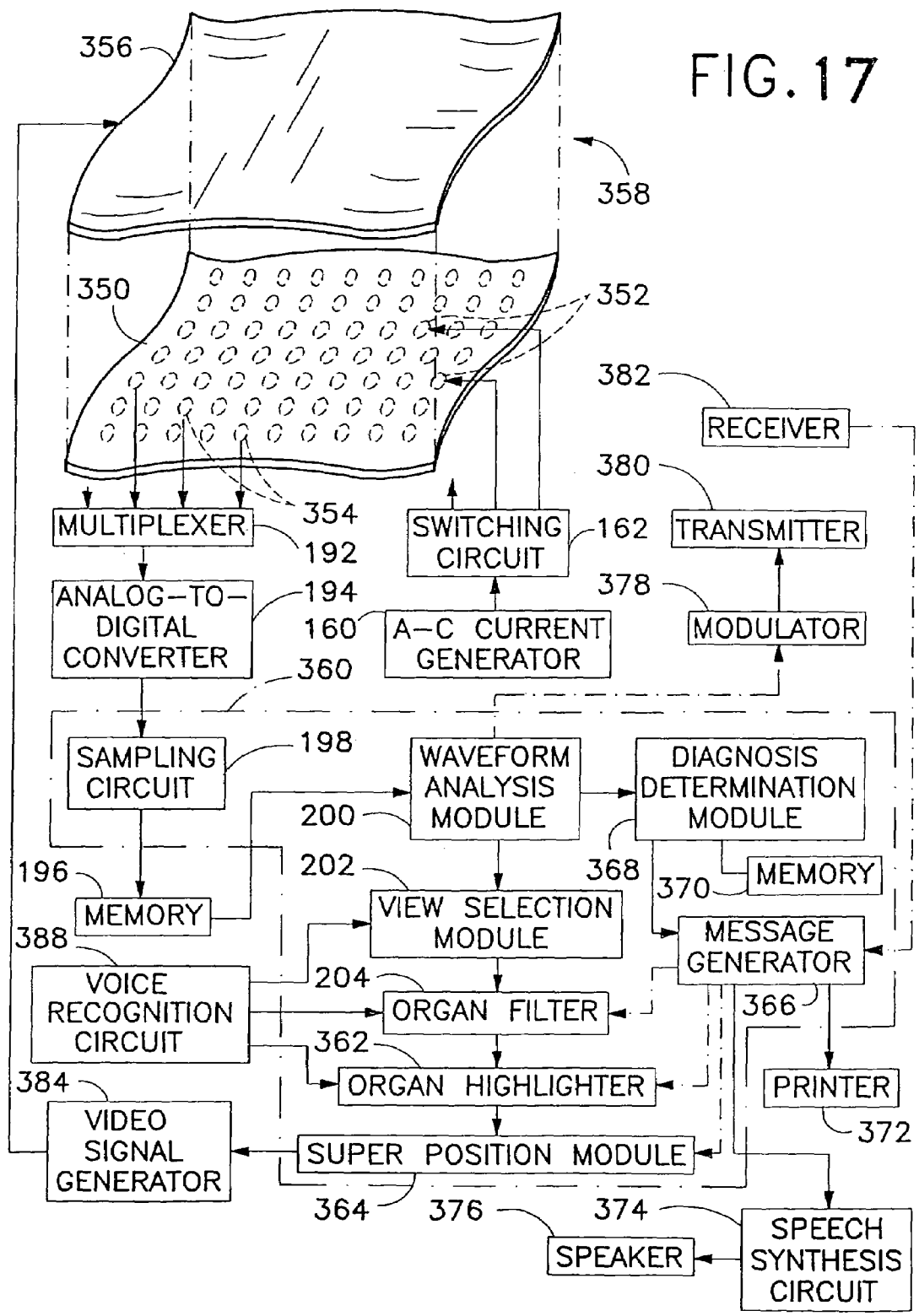
FIG. 17 is partially a schematic exploded perspective view and partially a block diagram of an ultrasonographic device or system related to the present invention.

As shown in FIG. 17, an ultrasonographic device or system with resonance therapy capability comprises a flexible substrate or web 350 which carries a plurality of piezoelectric electroacoustic transducers 352 and a plurality of piezoelectric acoustoelectric transducers 354. Transducers 352 are also used for resonance testing and treatment as discussed above with reference to FIGS. 1 and 2. A flexible video screen 356 is attached to substrate or web 350 substantially coextensively therewith. Video screen 356 may be implemented by a plurality of laser diodes (not shown) mounted in a planar array to a flexible carrier layer (not separately designated). The diodes are protected by a cover sheet (not separately illustrated) which is connected to the carrier layer. Energization componentry is operatively connected to the diodes for energizing the diodes in accordance with an incoming video signal to reproduce an image embodied in the video signal. In a video monitor, the laser diodes are tuned to different frequency ranges, so as to reproduce the image in color. The protective cover sheet may function also to disperse light emitted by the laser diodes, to generate a more continuous image.

Substrate or web 350 and video screen 356 comprise an ultrasonic video coverlet or blanket 358 which may be used with the control hardware depicted in FIGS. 7 and 8. Reference numerals used in FIGS. 7 and 8 are repeated in FIG. 17 to designate the same functional components.

Electroacoustic transducers 352 are connected to a-c or ultrasonic signal generator 160 for receiving respective a-c signals of different frequencies. Generator 160 produces different frequencies which are directed to the respective electroacoustic transducers 352 by switching circuit 162. Pressure waveforms of different ultrasonic frequencies have different penetration depths and resolutions and provide distinct amounts of information to a digital signal processor or computer 360. As discussed above with reference to computer 190 of FIG. 8, computer 360 is a specially programmed digital computer wherein functiorial modules are realized as generic digital processor circuits operating pursuant to preprogrammed instructions.

As discussed above with reference to FIG. 8, switching circuit or multiplexer 192 relays signals incoming from respective acoustoelectric transducers 354 in a predetermined intercalated sequence to analog-to-digital converter 194, the output of which is stored in computer memory 196 by sampling circuit 198. Wave analysis module 200 retrieves the digital data from memory 196 and processes the data to determine three dimensional organic structures inside a patient.

This three-dimensional structural data is provided to view selection module 202 for deriving two-dimensional images for display on video screen 256. Filter module 204 serves to remove selected organs, for example, overlying organs, from the image presented on video screen 356. Sampling circuit 198, wave analysis module 200, view selection module 202, and filter module 204 are program-modified generic digital circuits of computer 360.

Computer 360 contains additional functional modules, for example, an organ highlighter 362 and a superposition module 364. The functions of organ highlighter 362 are discussed above with reference to organ filter 176 and 204 in FIGS. 7 and 8. Organ highlighter 362 operates to provide a different color or intensity or cross-hatching to different parts of an image to highlight a selected image feature. For example, a tumor may be shown with greater contrast than the surrounding organ, thereby facilitating perception of the tumor on video screen 356. After organ filter 204 has removed selective internal tissues from an electronic signal representing or encoding an image of internal organs, highlighter 362 operates to highlight one or more features of the encoded image.

Computer 360 contains additional modules shown in FIG. 2 for detecting a resonant frequency or frequencies of a preselected internal tissue structure such as a tumor and for controlling the destruction of the tumor by energizing it with the detected resonant frequency or frequencies. As discussed above, the resonant frequency or frequencies selected for destroying the tumor do not appreciably or detrimentally affect other internal tissue structures of the patient.

Superposition module 364 effects the insertion of words or other symbols on the image displayed on video screen 356. Such words or symbols may, for example, be a diagnosis or alert signal produced by a message generator module 366 of computer 360 in response to a diagnosis automatically performed by a determination module 368 of computer 360. Module 368 receives the processed image information from waveform analysis module 200 and consults an internal memory 370 in a comparison or pattern recognition procedure to determine whether any organ or internal tissue structure of a patient has an abnormal configuration. In particular, determination module 368 may function in part to automatically detect lumps of tissue which have different pressure wave transmission characteristics than surrounding normal tissues, owing to a different tissue or cell density. The detection of such an abnormal configuration may be communicated to the physician by selectively removing organs, by highlighting organs or tissues, or superimposing an alphanumeric message on the displayed image. Accordingly, message generator 366 may be connected to organ filter 204 and organ highlighter 362, as well as to superposition module 364. The communication of an abnormal condition may be alternatively or additionally effectuated by printing a message via a printer 372 or producing an audible message via a speech synthesis circuit 374 and a speaker 376.

As discussed above, the ultrasonically derived three-dimensional structural information from waveform analysis module 200 may be transmitted over a telecommunications link (not shown in FIG. 17) via a modulator 378 and a transmitter 380. The transmitted information may be processed at a remote location, either by a physician or a computer, to generate a diagnosis. This diagnosis may be encoded in an electrical signal and transmitted from the remote location to a receiver 382. Receiver 382 is coupled with message generator module 366, which can communicate the diagnosis or other message as discussed above.

Computer 360 is connected at an output to a video signal generator 384 (which may be incorporated into the computer). Video signal generator 384 inserts horizontal and vertical synch signals and transmits the video signal to video screen 356 for displaying an image of internal patient organs thereon.

If a diagnosis made with the assistance of computer 360 identifies an internal tissue structure such as a tumor which requires destruction or obliteration, computer 360 is then operated to perform the testing and treatment procedures discussed above with reference to FIGS. 1 and 2.

Video screen 356, as well as other video monitors disclosed herein, may be a lenticular lens video display for presenting a stereographic image to a viewer. The ultrasonic processor, e.g., computer 190 or 360, operates to display a three-dimensional image of the internal organs on the lenticular lens video display 118. Because of the stereoscopic visual input a surgeon is provided via video display 356, he or she is better able to manipulate instruments and 212 during a surgical procedure. Lenticular lens video displays, as well as the operation thereof with input from two cameras, are disclosed in several U.S. patents, including U.S. Pat. No. 4,214,257 to Yamauchi and U.S. Pat. No. 4,164,748 to Nagata, the disclosures of which are hereby incorporated by reference.

It is to be noted that any of the ultrasonography devices or systems disclosed herein may be used in a robotic surgical procedure wherein one or more surgeons are at a remote location relative to the patient. The performance of robotic surgery under the control of the distant experts is disclosed in U.S. Pat. Nos. 5,217,003 and 5,217,453 to Wilk, the disclosures of which are hereby incorporated by reference. Video signals transmitted to the remote location may be generated by the analysis of ultrasonic waves as disclosed herein.

The ultrasonography devices or systems disclosed herein may be used in conjunction with other kinds of scanning devices, for example, spectral diagnosis and treatment devices described in U.S. Pat. Nos. 5,305,748 to Wilk and 5,482,041 to Wilk et al. (those disclosures incorporated by reference herein). It may be possible to incorporate the electromagnetic wave generators and sensors of those spectral diagnosis and treatment devices into the coverlet or blanket of the present invention.

As illustrated in FIG. 18, a medical imaging device comprises a planar firm substrate 404, a substantially flat video screen 406 provided on the substrate, and a flexible bag 408 connected to the substrate. Flexible bag 408 contains a fluidic medium such as water or gel capable of transmitting pressure waves of a wide range of frequencies including ultrasonic and sonic frequencies and is disposed on a side of the substrate opposite the video screen. As discussed above, a scanner 410 including an ultrasonic waveform generator 412 and a computer-implemented ultrasonic signal processor 414 is operatively connected to video screen 406 for providing a video signal thereto. The video signal encodes an image of internal tissues of a patient PT4 upon placement of medium-containing bag 408, substrate 404, and video screen 406 against the patient. The images of internal tissues and organs of the patient, including the stomach SH, the heart HT, the lungs LG, the small intestine SE, and the large intestine LE, are displayed on screen 406 at positions generally overlying the respective actual tissues and organs of the patient PT4.

Video screen 406 and substrate 404 may be provided with aligned apertures 415 for enabling the traversal of the video screen and the substrate by medical instruments as discussed above with reference to FIG. 18.

Figure 21A:
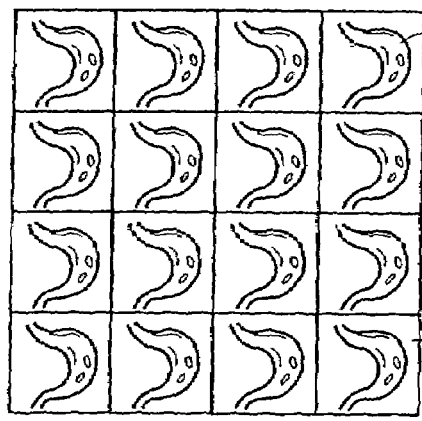
FIG. 21A is a schematic front elevational view of a video screen display configuration utilizable in the ultrasonographic device of FIGS. 19 and 20.
Figure 21B:
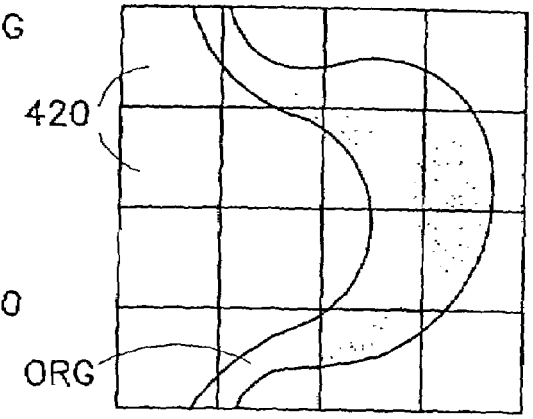
FIG. 21B is a schematic front elevational view of a further video screen display configuration utilizable in the ultrasonographic device of FIGS. 19 and 20.

FIGS. 19 and 20 show another medical imaging and treatment device comprising a flexible bag 416 containing a fluidic medium such as water or gel. A multiplicity of substantially rigid planar substrates or carrier pads 418 together with respective flat video screens 420 attached thereto are mounted to an upper surface of bag 416. Bag 416 serves in part to movably mount pads 418 with their respective video screens 420 to one another so that the orientations or relative angles of the video screen can be adjusted to conform to a curving surface of a patient PT5, as shown in FIG. 23. Again, a scanner 422 including an ultrasonic waveform generator 424 and a computer-implemented ultrasonic signal processor 426 is operatively connected to video screens 420 for providing respective video signals thereto. The video signals encode respective images of internal tissues of a patient PT5 upon placement of medium-containing bag 416, substrates 418 and video screens 420 against the patient. As illustrated in FIG. 21A, the video images displayed on screen 420 may be substantially the same, with differences in the angle of view of a target organ ORG, depending on the locations and orientations of the respective screens 420. Alternatively, in an enlarged view, a single image of the target organ ORG may be displayed, with each screen 420 displaying only a part of the total image. The technology for implementing these displays over video screens 420 is conventional and well known.

Scanners 410 and 422 are scanners with the same components as other scanners discussed herein, for example, with reference to FIG. 17. In brief, scanners 410 and 422 include components utilizing ultrasonic pressure waves for determining three-dimensional shapes of internal tissue structures and further include components utilizing pressure waves of generally lower frequencies for determining the mechanical resonant characteristics of the internal tissue structures and for destroying selected internal tissue structures through resonant loading. More specifically, scanners 410 and 422 each includes a plurality of electroacoustic transducers and a plurality of acoustoelectric transducers disposed in respective arrays along the respective bag 408 or 416 so that pressure waves can travel through the fluidic medium in the respective bag from the electroacoustic transducers and to the acoustoelectric transducers. Computers or processors 414 and 426 analyze incoming digitized sensor signals which are produced in response to pressure waves reflected from various tissue interfaces in the patient PT4 or PT5. From these incoming sensor signals, computers or processors 414 and 426 determine three-dimensional shapes of tissue interfaces and organs inside the patient PT4 or PT5 and also determine the mechanical resonant characteristics of detected internal tissue structures such as tumors.

As discussed above, it is recommended that markers be placed in prespecified locations on the patient to enable or facilitate an alignment of the displayed tissue representations and the respective underlying actual tissues. The markers are easily recognized by computer 426 and serve to define a reference frame whereby the positions and the orientations of the multiple video screens 420 relative to the patient's internal tissues are detectable. Thus, the position and the orientation of each video screen 420 relative to the internal tissues and organs of the patient PT5 are determined to enable the display on the video screens 420 of images of selected target tissues of the patient. The reference markers facilitate the display on screens 420 of respective views of the same organ or tissues from different angles depending on the positions and orientations of the various screens 420.

As discussed above, for example, with reference to FIG. 17, computers or processor 414 and 426 may include a module 362, typically realized as a programmed general computer circuit, for highlighting a selected feature (e.g., tumor) of the internal organs of patient PT4 or PT5. The highlighting is achievable by modifying the color or intensity of the selected feature relative to the other features in the displayed image, thus providing a visual contrast of the selected feature with respect to the other features of the displayed image. An intensity change may be effectuated by essentially blacking or whiting out the other portions of the image so that the selected feature is the only object displayed on the video screen.

The imaging devices of FIGS. 18 and 20 are optionally provided with a voice-recognition circuit 388 and a speech synthesis circuit 374 (FIG. 17) operatively connected to computer or processor 414 and 426. Advantages and uses of these components are discussed above with reference to FIG. 17. As further described above, computers or processors 414 and 426 are possibly programmed for automated diagnosis based on pattern recognition, with the computed diagnosis being communicated to the user physicians via speech synthesis circuit 374. The diagnosis capabilities include detecting and identifying possible tumors.

Figure 22:
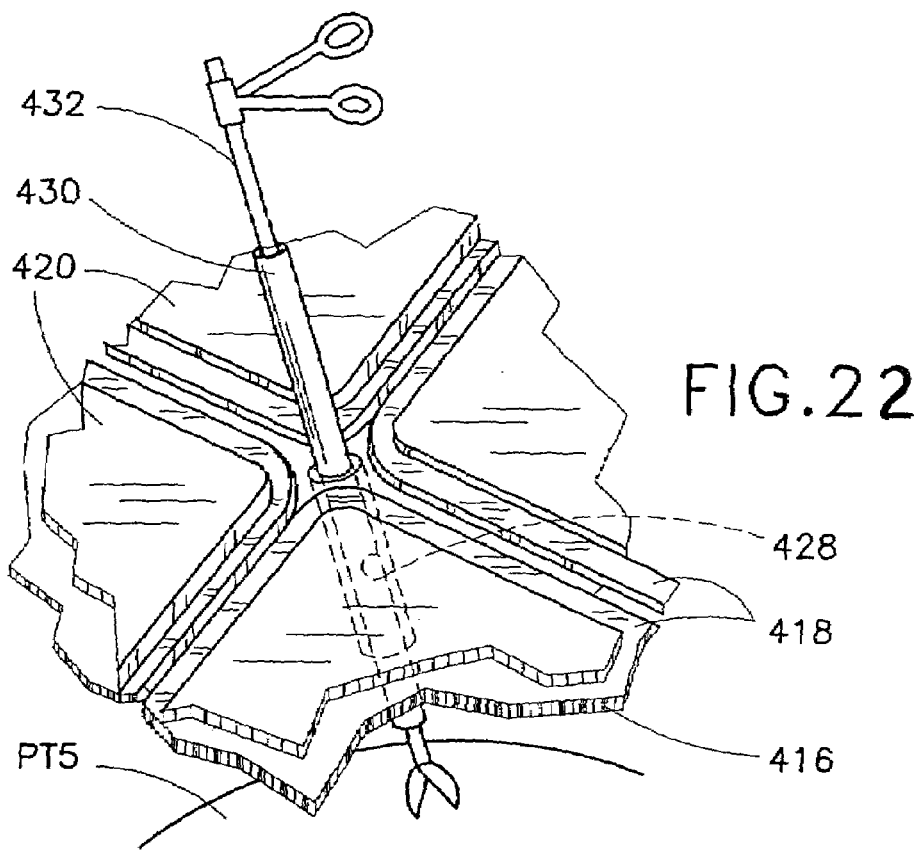
FIG. 22 is a schematic partial perspective view of a modification of the ultrasonographic device of FIGS. 19 and 20, showing a mode of use of the device in a surgical treatment or a diagnostic procedure.

As illustrated in FIG. 22, the imaging device of FIGS. 19 and 20 is advantageously provided with a plurality of apertures or passageways 428 extending through bag 416 in the interstitial spaces between video screens 420. Passageways 428 receive respective tubular cannulas 430 which extend both through the passageways and respective openings (not shown) in the skin and abdominal wall of the patient PT5. Medical instruments such as a laparoscopic forceps 432 or suction devices are inserted through passageways 428 for performing an operation on internal target tissues of patient PT5 essentially under direct observation as afforded by video screens 420. The distal ends of the medical instruments 432, inserted into patient PT5 in the field of view of the imaging system, are displayed on one or more video screens 420 together with internal target tissues of the patient. The uses of the imaging device of FIGS. 22 and 23 with passageways 428 as illustrated in FIG. 22 are substantially identical to the uses and modes of operation described above with reference to FIG. 9.

It is to be noted that bag 416 may be replaced by a plurality of bags (not illustrated) all filled with a fluidic medium through which ultrasonic pressure waves may be transmitted. Each planar substrate or carrier pad 418 and its respective video screen may be attached to a respective fluid-filled bag. In this modification of the ultrasonographic device of FIGS. 18 and 20, apertures performing the function of passageways 428 (FIG. 22) are naturally formed as gaps or spaces between adjacent bags. Separate coupling elements (not illustrated) must be provided between adjacent video screens 420 for forming an integral structure while enabling at least limited flexing between adjacent video screens 420.

It is to be additionally understood that substrates 418 may be formed as carrier layers for active picture elements of video screens 420 and may be visually indistinguishable from the video screens 420.

The imaging devices of FIGS. 18 and 19, 20 may include a transmitter 380 and a receiver 382 (FIG. 17) for operatively connecting scanners 410 and 422 and particularly computers or processors 414 and 426 to a long-distance hard-wired or wireless telecommunications link. As pointed out above, image data transmitted over the telecommunications link to a video monitor at a remote location will enable observation of the patient's internal tissues by distant specialists who may also operate on the patients robotically via the telecommunications link.

The determination of a maximally destructive frequency for a given tissue mass, as described above, may be understood in terms of measurement of internal friction $Q^{-1}$, as will be comprehended by those skilled in the art. Peaks in a frequency plot of $Q^{-1}$ correspond to frequencies of maximum energy absorption, hence maximum potential tissue destruction.

Although the invention has been described in terms of particular embodiments and applications, one of ordinary skill in the art, in light of this teaching, can generate additional embodiments and modifications without departing from the spirit of or exceeding the scope of the claimed invention. For example, the pressure waves energizing a tumor for purposes of resonant disintegration in accordance with the present invention may be generated by one or more transducers disposed inside the patient. These transducers may be piezoelectric crystals mounted to the ends of rods inserted via cannulas as described above with reference to FIG. 4. Those transducers may be provided at the distal ends of respective rods or wires inserted into the patient transdermally or percutaneously or intravascularly. Accordingly, it is to be understood that the drawings and descriptions herein are proffered by way of example to facilitate comprehension of the invention and should not be construed to limit the scope thereof.

What is claimed is:

1. A method for treating cancer, comprising:
   detecting a tumor in a patient; and
   applying mechanical pressure waves to said tumor at a mechanical resonance frequency of the entire tumor as a unitary body, to effectively destroy said tumor,
   the applying of said mechanical pressure waves to said tumor including disposing at least one transducer in the patient and energizing said transducer to generate said mechanical pressure waves.

2. A method for treating cancer, comprising:
   detecting a tumor in a patient;
   applying mechanical pressure waves to said tumor at a mechanical resonance frequency of the entire tumor as a unitary body, to effectively destroy said tumor; and
   determining said mechanical resonance frequency, the determining of said mechanical resonance frequency including:
   generating a series of investigatory pressure waves of respective different preselected frequencies in a patient so that said investigatory pressure waves are transmitted to said tumor through overlying tissues;
   during the generating of said investigatory pressure waves in the patient, monitoring responsive oscillatory motion of said tumor and at least some internal tissues of the patient proximate to the tumor, said responsive oscillatory motion arising as a result of the transmission of said investigatory pressure waves into the patient; and
   determining said mechanical resonance frequency from the responsive oscillatory motion of said tumor and said internal tissues, said mechanical resonance frequency being a pressure wave frequency which results in a resonant loading of said tumor and essentially leaves said internal tissues undamaged.

3. The method defined in claim 2 wherein the applying of the mechanical pressure waves to said tumor includes generating, in the patient, treatment pressure waves of said mechanical resonance frequency and of an effective amplitude so that said tumor resonates with sufficient energy to mechanically destroy said tumor.

4. The method defined in claim 3 wherein the generating of said treatment pressure waves includes placing an electromechanical transducer in contact with an external surface of the patient and energizing said transducer with a periodic voltage of said mechanical resonance frequency.

5. The method defined in claim 3 wherein the generating of said treatment pressure waves includes placing a substrate in contact with an external surface of the patient, said substrate carrying plurality of electromechanical transducers, and further includes energizing said transducers with a periodic voltage of said mechanical resonance frequency.

6. The method defined in claim 3 wherein the generating of said investigatory pressure waves includes placing a substrate in contact with an external surface of the patient, said substrate carrying a plurality of electromechanical transducers, and further includes energizing said transducers with periodic voltages of said different preselected frequencies.

7. The method defined in claim 6 wherein the energizing of said transducers includes energizing each of said transducers with voltages of a plurality of different frequencies, the monitoring of responsive oscillatory motion of said tumor and at least some internal tissues of the patient proximate to the tumor including monitoring responsive oscillatory motion of said tumor and said internal tissues proximate to said tumor for each of said transducers and each of the frequencies with which the respective transducers are energized.

8. The method defined in claim 7 wherein the patient has skin surfaces in different planes and wherein the placing of said substrate in contact with an external surface of the patient includes positioning at least one of said transducers in pressure-wave transmitting contact with each of said skin surfaces.

9. The method defined in claim 7 wherein the generating of said treatment pressure waves includes energizing at least one of said transducers with a periodic voltage of said determined pressure wave frequency.

10. The method defined in claim 6 wherein the patient has skin surfaces in different planes and wherein the placing of said substrate in contact with an external surface of the patient includes positioning at least one of said transducers in pressure-wave transmitting contact with each of said skin surfaces.

11. The method defined in claim 2 wherein the monitoring of motion of said tumor and said internal tissues includes:
    sensing pressure waves generated at a skin surface of the patient in response to motion of said tumor and said internal tissues; and
    processing said pressure waves to determine said responsive oscillatory motion of said tumor.

12. The method defined in claim 11 wherein the processing of said pressure waves includes analyzing said pressure waves to determine three-dimensional shapes of internal tissue structures including said tumor and to determine modes and magnitudes of motions of said internal tissues structures.

13. The method defined in claim 2 wherein the generating of said investigatory pressure waves includes placing an electromechanical transducer in contact with an external surface of the patient and energizing said transducer with periodic voltages of said different preselected frequencies.

14. The method defined in claim 2 wherein the monitoring of motion of said tumor and said internal tissues includes:
    providing a multiplicity of probes each having sensors for determining motion;
    inserting said probes into the patient; and
    monitoring signal outputs of said sensors to determine motion of surfaces or boundaries of said tumor and said internal tissues.

15. The method defined in claim 2 wherein the applying of said mechanical pressure waves to said tumor includes transmitting said mechanical pressure wave through overlying tissues of the patient.

16. A medical treatment system comprising:
    a carrier;
    a plurality of electromechanical transducers mounted to said carrier;
    an a-c current generator operatively connected to at least some of said transducers for energizing said transducers with electrical signals of a plurality of pre-established frequencies to produce first pressure waves in the patient; and
    an acoustic signal processor operatively connected to at least some of said transducers programmed to analyze incoming pressure waves to determine mechanical resonant characteristics of internal tissue structures of a patient, said incoming pressure waves being generated by said internal tissue structures in response to said first pressure waves, said processor being programmed more particularly to determine which of said transducers is to be energized with which of said frequencies to resonantly overload a predetermined one of said tissue structures, thereby mechanically destroying said one of said tissue structures.

17. The system defined in claim 16, further comprising means operatively connected to said processor for identifying said one of said tissue structures.

18. The system defined in claim 17 wherein said means for identifying includes:
    at least one electroacoustic transducer mounted to said carrier for producing primary ultrasonic pressure waves in the patient;
    at least one acoustoelectric transducer mounted to said carrier for sensing secondary ultrasonic pressure waves produced at said internal tissue structures in response to said primary pressure waves; and
    an ultrasonic wave analyzer operatively connected to said acoustoelectric transducer for determining three-dimensional shapes of said internal tissue structures of the patient by analyzing signals generated by said acoustoelectric transducer in response to said secondary pressure waves.

19. The system defined in claim 18 wherein said electro acoustic transducer is one of said electromechanical transducers and wherein said acousto electric transducer is one of said electromechanical transducers.

20. The system defined in claim 18 wherein said carrier includes a flexible web conformable to the patient.

21. The system defined in claim 18, further comprising a video monitor linked to said analyzer for displaying an image of said internal tissue structures.

22. A method for performing a medical operation, comprising:
    placing a plurality of electromechanical transducers in pressure-wave-transmitting contact with a patient;
    energizing at least some of said transducers with an ultrasonic frequency to produce ultrasonic first pressure waves in the patient;
    energizing at least one of said transducers with another frequency in a range below ultrasonic to produce second pressure waves in the patient; and
    analyzing ultrasonic third pressure waves produced at internal tissue structures of the patient in response to said first pressure waves to determine three dimensional shapes of said tissue structures and to monitor resonant motion of said tissue structures in response to said second pressure waves.

23. The method defined in claim 22 wherein said one of said transducers is energized in seriatim with a plurality of test frequencies in said range below ultrasonic, said another frequency being one of said test frequencies, the analyzing of said third pressure waves including determining whether any of said test frequencies results in a resonant loading of a predetermined one of said tissue structures.

24. The method defined in claim 22, further comprising, upon determining that one of said test frequencies is a resonant frequency of said predetermined one of said tissue structures, energizing said transducer with said one of said test frequencies to destroy said predetermined one of said tissue structures.

25. The method defined in claim 22 wherein said transducers are all attached to a single flexible substrate, the placing of said transducers in pressure-wave-transmitting contact with the patient including conforming at least a portion of said substrate to the patient.

26. The method defined in claim 22, further comprising energizing a plurality of said transducers in seriatim with a plurality of test frequencies in said range below ultrasonic, the analyzing of said third pressure waves including identifying which of said transducers and which of said test frequencies, if any, induce a resonant loading of said predetermined one of said tissue structures.

27. The method defined in claim 22 wherein the analyzing of said third pressure waves to monitor resonant motion of said tissue structures in response to said second pressure waves includes automatically comparing sizes and shapes of said tissue structures at a succession of times to determine changes in sizes and shapes of said tissue structures.

* * * * *